(12) United States Patent
Esses

(10) Patent No.: US 9,408,936 B2
(45) Date of Patent: Aug. 9, 2016

(54) AIR FRESHENER

(71) Applicant: Alfred Esses, Brooklyn, NY (US)

(72) Inventor: Alfred Esses, Brooklyn, NY (US)

(73) Assignee: Alfred Esses, Brooklyn, NY (US)

( * ) Notice: Subject to any disclaimer, the term of this patent is extended or adjusted under 35 U.S.C. 154(b) by 39 days.

(21) Appl. No.: 14/341,382

(22) Filed: Jul. 25, 2014

(65) Prior Publication Data

US 2016/0022855 A1     Jan. 28, 2016

(51) Int. Cl.
| | | |
|---|---|---|
| *A61L 9/00* | (2006.01) | |
| *A62B 7/08* | (2006.01) | |
| *A01G 13/06* | (2006.01) | |
| *A61L 9/03* | (2006.01) | |
| *B60H 3/00* | (2006.01) | |

(52) U.S. Cl.
CPC .............. *A61L 9/03* (2013.01); *B60H 3/0007* (2013.01)

(58) Field of Classification Search
CPC .............. A61L 9/00; A61L 9/03; A61L 9/037
USPC .......... 422/1, 5, 123, 125, 306; 392/386, 391, 392/394
See application file for complete search history.

(56) References Cited

U.S. PATENT DOCUMENTS

| | | | |
|---|---|---|---|
| 3,872,280 A * | 3/1975 | Van Dalen ................ | A61L 9/03 128/203.27 |
| 6,099,137 A | 8/2000 | McCormack | |
| 7,687,037 B2 | 3/2010 | Wheatley et al. | |
| 7,687,038 B2 | 3/2010 | Wheatley et al. | |
| 8,480,960 B2 | 7/2013 | Wheatley et al. | |
| 8,662,480 B1 | 3/2014 | Irvin | |
| 8,673,223 B1 | 3/2014 | Finlay | |
| 2014/0112649 A1 | 4/2014 | Irvin et al. | |
| 2014/0158789 A1 | 6/2014 | Haymond | |
| 2014/0161672 A1 | 6/2014 | Wheatley et al. | |

FOREIGN PATENT DOCUMENTS

| | | |
|---|---|---|
| CN | 200947724 Y | 9/2007 |
| CN | 202950996 U | 5/2013 |
| GB | 2292271 A | 2/1996 |

* cited by examiner

*Primary Examiner* — Monzer R Chorbaji
(74) *Attorney, Agent, or Firm* — Moritt Hock & Hamroff LLP; Steven S. Rubin, Esq.

(57) ABSTRACT

Technologies are generally described for air freshener devices. The devices may comprise an insertion section including electrodes. The electrodes may be effective to receive and conduct an electric current and to secure the devices to an electric source. The devices may include a base. The base may be attached the insertion section. The base may include a port effective to receive at least part of the electric current from the electrodes. The base may include a collar effective to apply heat sufficient to release a fragrance from a material infused with the fragrance when at least part of the electrical current is supplied to the collar from the electrodes. The device may include a cap. The cap may have a ring shaped cross-section and may be sized and shaped so as to be connectable to the base such that the port is accessible when the cap is connected.

20 Claims, 3 Drawing Sheets

AIR FRESHENER

BACKGROUND

Air fresheners reduce or mask undesired odors and emit pleasant odors. Air fresheners typically emit a pleasant odor in the form of a fragrance. Air fresheners include sprays, candles, oils, gels, and plug-ins.

SUMMARY OF THE INVENTION

In one example, air freshener devices are generally described. The devices may comprise an insertion section. The insertion section may include a first side and a second side. The insertion section may include electrodes. The electrodes may be effective to receive and conduct an electric current. The electrodes may be further effective to secure the device to an electric source such that the first side of the insertion section is proximate to the electric source. The devices may include a base. The base may include a first end. The first end of the base may be attached to the second end of the insertion section. The base may include a port at a second end of the base. The port may be effective to receive at least part of the electric current from the electrodes. The base may include a collar. The collar may be within the base. The collar may be positioned between the first end of the base and the second end of the base. The collar may be effective to apply heat sufficient to release a fragrance from a material infused with the fragrance when at least part of the electrical current is supplied to the collar from the electrodes. The devices may include a cap. The cap may have a ring shaped cross-section. The cap may be sized and shaped so as to be connectable to the base around the second end of the base such that the port is accessible when the cap is connected to the base.

In another example, methods for assembling a device are generally described. The methods may comprise attaching a cap to a first end of a base. The cap may have a ring shaped cross section. The cap may be effective to secure a material infused with a fragrance to a collar and the base. The base may include a port at the first end of the base. The collar may be positioned between the first end of the base and the second end of the base. The first end of the base may be connected to a first side of an insertion section. The insertion section may include electrodes effective to receive and conduct an electric current. The electrodes may be further effective to secure the device to an electric source such that a second side of the insertion section is proximate to the electric source. The port may be effective to receive at least part of the electric current from the electrodes. The collar may be effective to apply heat sufficient to release the fragrance from the material infused with the fragrance when at least part of the electrical current is supplied to the collar from the electrodes.

In another example, methods for releasing fragrance from a material are generally described. The methods may comprise placing a material infused with a fragrance around a collar. The collar may be positioned between a first end of a base and a second end of the base. The first end of the base may be attached to a first side of an insertion section. The insertion section may include electrodes effective to receive and conduct an electric current. The electrodes may be further effective to secure a device to an electric source such that a second side of the insertion section is proximate to the electric source. The methods may comprise attaching a cap to the second end of the base. The cap may have a ring shaped cross section. The cap may be effective to secure the material infused with the fragrance to the collar and the base. The methods may comprise attaching the electrodes to the electric source. The methods may comprise receiving the electric current from the electrodes at the collar. The collar may be effective to apply heat sufficient to release the fragrance from the material infused with the fragrance.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and other features of this disclosure will become more fully apparent from the following description and appended claims taken in conjunction with the accompanying drawings. Understanding that these drawings depict only some embodiments in accordance with the disclosure and are therefore not to be considered limiting of its scope, the disclosure will be described with additional specificity and detail by reference to the accompanying drawings in which:

Figure 1:
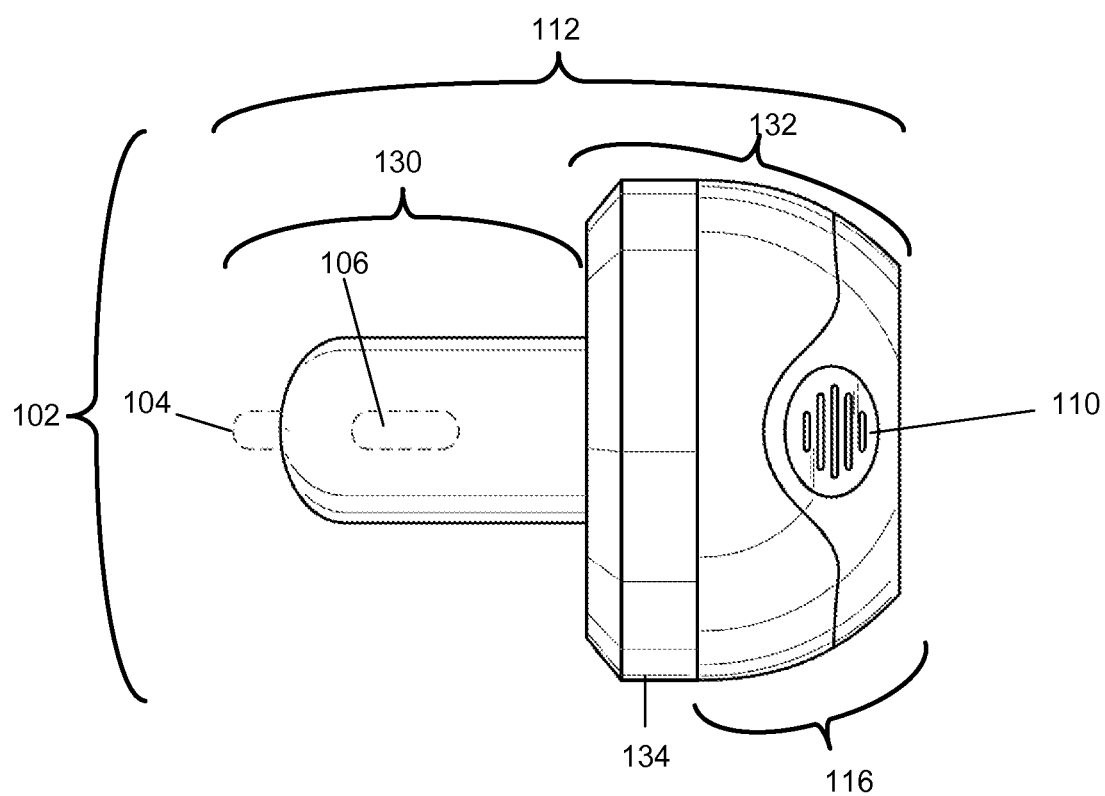
FIG. 1 is a side view of an air freshener.

all in accordance with an embodiment of the invention.

DETAILED DESCRIPTION

In the following detailed description, reference is made to the accompanying drawings which form a part thereof. In the drawings, similar symbols typically identify similar components unless context indicates otherwise. The illustrative embodiments described in the detailed description, drawings and claims are not meant to be limiting. Other embodiments may be utilized and other changes may be made without departing from the spirit or scope of the subject matter presented herein. It will be readily understood that the aspects of the present disclosure as generally described herein and as illustrated in the accompanying figures can be arranged, substituted, combined, separated and/or designed in a wide variety of different configurations all of which are explicitly contemplated herein.

FIG. 1 is a side view of an air freshener in accordance with an embodiment of the invention. An air freshener 102 may include a body 112 comprising an insertion section 130 connected to an outer section 132. Insertion section 130 of body 112 may have a cylindrical shape and may have a first and a second end. Insertion section 130 may include an anode electrode 104 extending axially from the first end. The second end of insertion section 130 may be connected to outer section 132. Insertion section 130 may include cathode electrodes 106 extending radially from the sides of insertion section 130. Insertion section 130 including anode electrode 104 and cathode electrodes 106, may be arranged such that air freshener 102 may be plugged into a cigarette lighter socket, such as a vehicle cigarette lighter socket, with the anode electrode 104 and the cathode electrodes 106 aligning and connecting to the electrodes of the vehicle cigarette lighter socket respectively. The current provided by the vehicle cigarette lighter socket may be direct current and may be 12 volts.

Outer section 132 may be substantially hemispherical shaped and include a cap 116 and a base 134. Outer section 132 may be connected to insertion section 130 axially at base 134. Base 134 may be substantially cylindrically shaped with a substantially larger radius than insertion section 130. Base 134 may have a first and a second side and may include flat edges, textured edges or be smooth. Base 134 may slightly taper in radius axially on the first side of base 134. The first side of base 134 may be attached to the second side of insertion section 130. Cap 116 may extend axially from base 134 on the second side of base 134. Cap 116 may be substantially hemispherical in shape and may be smooth and taper in radius along an axial direction away from base 134. Cap 116 may have a ring shaped cross-section defining an opening in the middle of cap 116 where the second end of base 134 may be exposed when cap 116 is connected to base 134. Cap 116 may include vents 110. Vents 110 may be grilled, slotted, screened, or any other venting configuration capable of allowing air to flow between inside of cap 116 and outside of cap 116.

Figure 2:
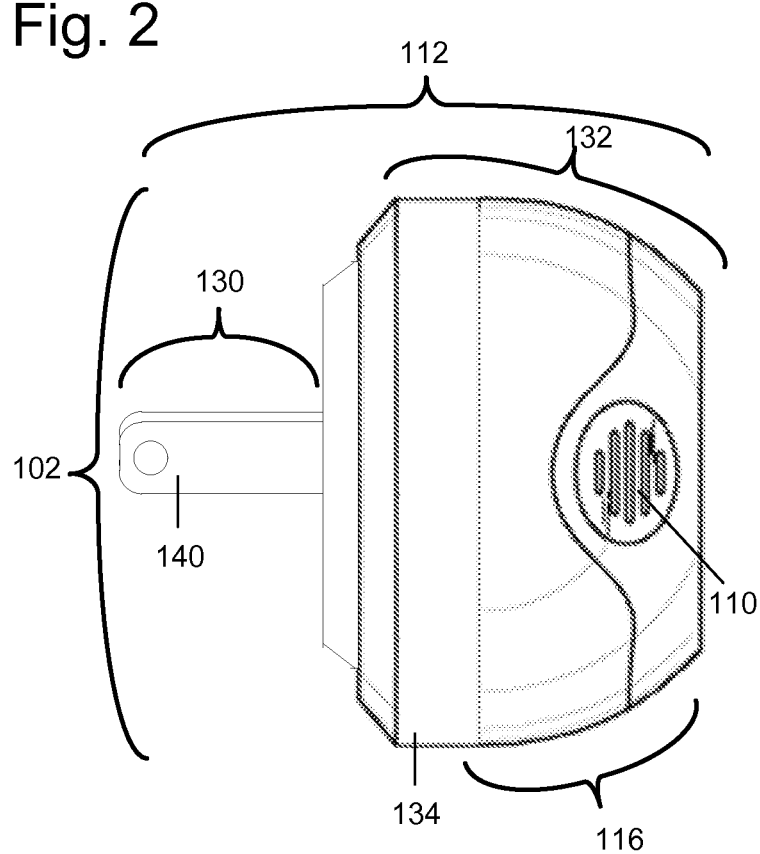
FIG. 2 is a side view of an air freshener with metal terminals.

FIG. 2 is a side view of air freshener 102 with metal terminals in accordance with an embodiment of the invention. Those components in FIG. 2 that are labeled identically to components of FIG. 1 will not be described again for the purposes of clarity. In another embodiment, insertion section 130 may include electrodes 140 that are metal prongs or terminals extending axially from base 134. Metal terminals 140 may be arranged such that air freshener 102 may be plugged into an electrical socket. Metal terminals 140 may secure air freshener 102 to an electric socket when plugged into the electric socket. An electrical current may be provided to metal terminals 140 and subsequently to air freshener 102 when metal terminals 140 are plugged into an electrical socket.

Figure 3:
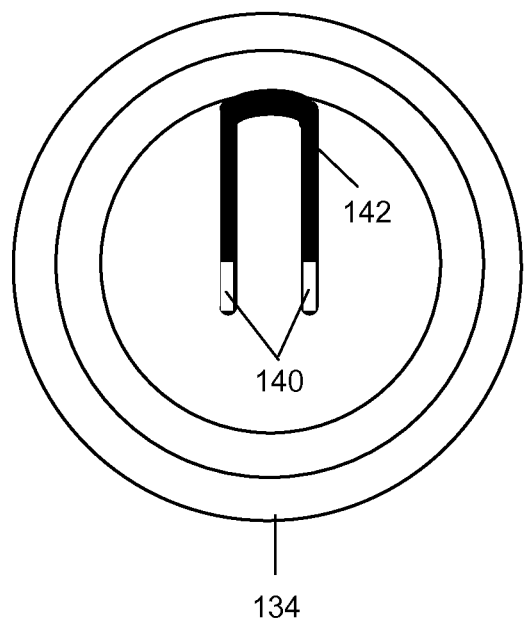
FIG. 3 is a rear view of an air freshener with metal terminals.

FIG. 3 is a rear view of air freshener 102 with metal terminals in accordance with an embodiment of the invention. Those components in FIG. 3 that are labeled identically to components of FIGS. 1-2 will not be described again for the purpose of clarity. Metal terminals 140 in insertion section 130 may be retractable. Metal terminals 140 may be able to fold 90 degrees to range from perpendicular to the surface of the first side of base 134 to parallel to the surface of the first side of base 134. Grooves 142 may be present in the surface of base 134 such that metal terminals 140, when folded parallel to the surface of the first side of base 134, may recess into the surface of the first side of base 134. When recessed into the surface of the first side of base 134, metal terminals 140 may be completely submerged within the first side of base 134.

Figure 4:
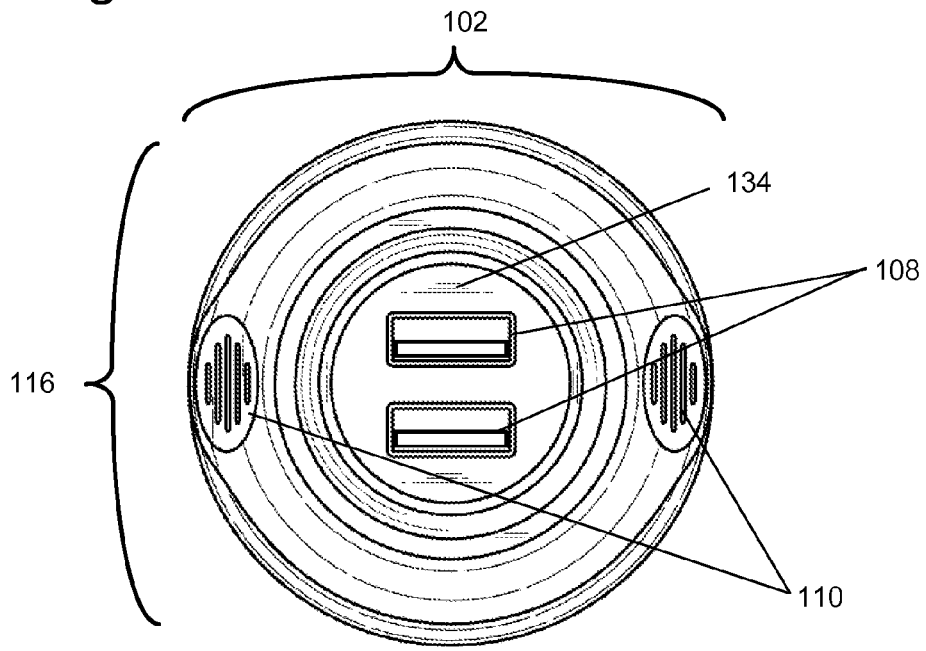
FIG. 4 is a front view illustrating two ports of an air freshener.

FIG. 4 is a front view illustrating two ports of air freshener 102 in accordance with an embodiment of the invention. Those components in FIG. 4 that are labeled identically to components of FIGS. 1-3 will not be described again for the purposes of clarity. Air freshener 102 may include ports 108 and grilled vents 110. Ports 108 may be included in the second side of base 134 and grilled vents 110 may be included in cap 116. Ports 108 may be universal serial bus (USB) ports and may be accessible when cap 116 is attached to base 134. Cap 116 may have a ring shaped cross-section and may be sized and shaped so as to be connectable to base 134 around the second end of base 134 such that ports 108 are accessible when cap 116 is connected. In one embodiment, ports 108 may be powered by an electric current from anode electrode 104 and cathode electrode 106 (illustrated in FIG. 1) when connected to vehicle cigarette lighter socket electrodes. In another embodiment, ports may be powered by an electric current from metal terminals 140 (illustrated in FIGS. 2-3) when plugged into an electric socket. As described in more detail below, vents 110 in cap 116 may allow fragrance to flow from air freshener 102.

Figure 5:
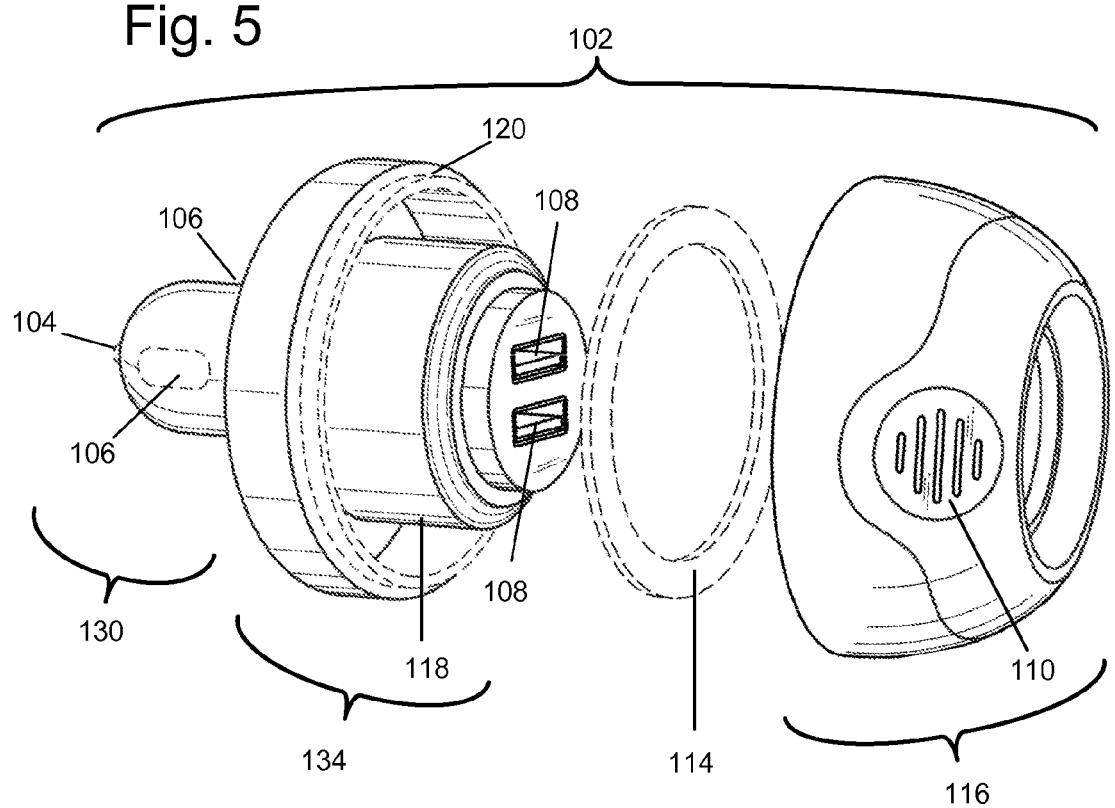
FIG. 5 is an angled side perspective view illustrating a body, a disk, and a cap enclosure of an air freshener.

FIG. 5 is an angled side perspective view illustrating a body, a disk, and a cap enclosure of car air freshener 102 in accordance with an embodiment of the invention. Those components in FIG. 5 that are labeled identically to components of FIG. 1-4 will not be described again for the purposes of clarity. Air freshener 102 may include insertion section 130, base 134, a disk 114 and cap 116. Insertion section 130 may include anode electrode 104 and cathode electrodes 106, and may be attached to base 134. Base 134 may include USB ports 108, and collar 118. Current provided by a vehicle cigarette lighter socket may travel from electrode cathode 106 to electrode anode 104 and provide power to USB ports 108.

Disk 114 may be a liquid oil, gel or solid material infused with a fragrance. Fragrances may be any desirable fragrance including fruit scents, new car smell, etc. Disk 114 may be in the shape of a flat ring and may fit around collar 118. Collar 118 may be heated when a current provided by vehicle cigarette lighter socket travels from electrode cathode 106 to electrode anode 104. Heating of collar 118 by electric current provided by vehicle cigarette lighter socket may release fragrance from disk 114.

Cap 116 may secure disk 114 to collar 118 and base 134 when cap 116 is attached to base 134. Cap 116 may attach to base 134 and be secured to base 134 by locking mechanism 120. Locking mechanism 120 may secure cap 116 to base 134 such as by protrusions from base 134 that cap 116 may snap onto to secure to base 134. Locking mechanism 120 may secure cap 116 to base 134 such as by threads on base 134 for cap 116 to screw onto to secure to base 134. Fragrance emitted from heating of disk 114 may disperse through vents 110 in cap 116 to freshen air proximate to air freshener 102.

For example, insertion section 130 may be placed into a vehicle cigarette lighter socket such that anode electrode 104 and cathode electrodes 106 align with electrodes in vehicle cigarette lighter socket. Electric current may travel from vehicle cigarette lighter socket to cathode electrodes 106 through air freshener 102 circuitry to anode electrode 104 and back to vehicle cigarette lighter socket. Electric current may be direct current and may be 12 volts. Air freshener 102 circuitry may be configured to supply electric current to USB ports 108. USB ports 108 may function to supply power to connected USB cables for powering and/or charging devices attached to a connected USB cable. Air freshener 102 circuitry may further be configured to provide electric current to heat collar 118 in base 134. Collar 118 may be heated by electric current as current travels from cathode electrodes 106 to anode electrode 106. Collar 118, heated by electric current, may conduct heat to disk 114 located and secured around collar 118 by cap 116. Heating of disk 114 may release fragrance infused within material of disk 114. Released fragrance may diffuse into the air. Air with diffused fragrance may disperse through vents 110 and provide fragrance to air proximate to air freshener 102.

Among other potential benefits, a device in accordance with the disclosure may provide a desired fragrance within a vehicle while also providing operational USB ports for use. Vehicles with a single cigarette lighter socket may be able to utilize the single socket for more than one purpose. Multiple devices, such as global positioning devices (GPS), cell phone chargers, media players, etc., may be attached to the USB ports while freshening the air of the vehicle.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A device comprising:
an insertion section, wherein the insertion section includes:
a first side and a second side;
electrodes wherein the electrodes are effective to receive and conduct an electric current and further effective to secure the device to an electric source such that the first side of the insertion section is proximate to the electric source;
a base, a first end of the base attached to the second end of the insertion section, the base includes:
a port at a second end of the base, the port effective to receive at least part of the electric current from the electrodes and supply power to an additional device attached to the port;
a collar within the base, positioned between the first end of the base and the second end of the base, wherein the collar is effective to apply heat sufficient to release a fragrance from a solid material infused with the fragrance when at least part of the electrical current is supplied to the collar from the electrodes; and
a cap, where the cap has a ring shaped cross-section and is sized and shaped so as to be connectable to the base around the second end of the base such that the port is accessible when the cap is connected to the base.

2. The device of claim 1, wherein the electrodes are configured to align and connect to electrodes of a vehicle cigarette lighter socket.

3. The device of claim 1, wherein the electrodes are configured to align and connect to electrodes in an electric outlet.

4. The device of claim 1, wherein the solid material infused with the fragrance is in the shape of a flat ring.

5. The device of claim 1, wherein the cap includes a vent effective to disperse the fragrance.

6. The device of claim 1, wherein:
the base includes protrusions on the second side of the base; and
the cap is effective to snap onto the protrusions so that the cap is secured to the base.

7. The device of claim 1, wherein:
the base includes threads on the second side of the base; and
the cap is effective to be screwed onto the threads so that the cap is secured to the base.

8. The device of claim 1, wherein:
the electrodes are configured to align and connect to electrodes of a vehicle cigarette lighter socket;
the solid material infused with the fragrance is in the shape of a flat ring; and
the cap includes a vent effective to disperse the fragrance.

9. The device of claim 8, wherein:
the base includes threads on the second side of the base; and
the cap is effective to be screwed onto the threads so that the cap is secured to the base.

10. A method for assembling a device, the method comprising:
attaching a cap to a first end of a base, the cap having a ring shaped cross section and effective to secure a solid material infused with a fragrance to a collar and the base, wherein:
the base includes a port at the first end of the base and the collar is positioned between the first end of the base and the second end of the base, the first end of the base being connected to a first side of an insertion section;
the insertion section includes electrodes effective to receive and conduct an electric current and the electrodes are further effective to secure the device to an electric source such that a second side of the insertion section is proximate to the electric source;
the port effective to receive at least part of the electric current from the electrodes and supply power to an additional device attached to the port; and
the collar effective to apply heat sufficient to release the fragrance from the solid material infused with the fragrance when at least part of the electrical current is supplied to the collar from the electrodes.

11. The method of claim 10, wherein the electrodes are configured to align and connect to electrodes of a vehicle cigarette lighter socket.

12. The method of claim 10, wherein the electrodes are configured to align and connect to electrodes in an electric outlet.

13. The method of claim 10, wherein the solid material infused with the fragrance is in the shape of a flat ring.

14. The method of claim 10, wherein the cap includes a vent effective to disperse the fragrance.

15. The method of claim 10, further comprising attaching the cap to the first end of the base with a locking mechanism, wherein the locking mechanism includes protrusions from the first end of the base and the cap is effective to snap onto the protrusions so that the cap is secured to the base.

16. The method of claim 10, further comprising attaching the cap to the first end of the base with a locking mechanism, wherein the locking mechanism includes threads on the first end of the base and the cap screws onto the threads to secure the cap to the base.

17. The method of claim 10, wherein:
the electrodes are configured to align and connect to the electrodes of a vehicle cigarette lighter socket;
the solid material infused with the fragrance is in the shape of a flat ring; and
the cap includes a vent effective to disperse the fragrance.

18. The method of claim 17, further comprising attaching the cap to the first end of the base with a locking mechanism, wherein the locking mechanism includes threads on the first end of the base and the cap screws onto the threads to secure the cap to the base.

19. The method of claim 10, wherein:
the electrodes are configured to align and connect to an electric outlet;
the solid material infused with the fragrance is in the shape of a flat ring; and
the cap includes a vent effective to disperse the fragrance.

20. A method for releasing fragrance from a solid material and powering a device, the method comprising:
placing a solid material infused with a fragrance around a collar positioned between a first end of a base and a second end of the base, the first end of the base attached to a first side of an insertion section, the insertion section including electrodes effective to receive and conduct an electric current and further effective to secure a device to an electric source such that a second side of the insertion section is proximate to the electric source;
attaching a cap to the second end of the base, the cap having a ring shaped cross section and effective to secure the solid material infused with the fragrance to the collar and the base;
attaching the electrodes to the electric source;

receiving a first portion of the electric current from the electrodes at the collar wherein the collar is effective to apply heat sufficient to release the fragrance from the solid material infused with the fragrance and receiving a second portion of the electric current from the electrodes at a port wherein the port is effective to supply power to a device attached to the port.

* * * * *